US012805817B2

(12) United States Patent
Wang et al.

(10) Patent No.: US 12,805,817 B2
(45) Date of Patent: Nov. 24, 2026

(54) DATA ACQUISITION SYSTEM ASSEMBLY, GANTRY OF MEDICAL IMAGING SYSTEM, AND MEDICAL IMAGING SYSTEM

(71) Applicant: GE Precision Healthcare LLC, Waukesha, WI (US)

(72) Inventors: Xiaowei Wang, Beijing (CN); Weimin Qu, Beijing (CN)

(73) Assignee: GE Precision Healthcare LLC, Waukesha, WI (US)

( * ) Notice: Subject to any disclaimer, the term of this patent is extended or adjusted under 35 U.S.C. 154(b) by 125 days.

(21) Appl. No.: 18/891,887

(22) Filed: Sep. 20, 2024

(65) Prior Publication Data

US 2025/0099054 A1 Mar. 27, 2025

(30) Foreign Application Priority Data

Sep. 22, 2023 (CN) ........................ 202311235845.4

(51) Int. Cl.
*A61B 6/03* (2006.01)
*A61B 6/58* (2024.01)

(52) U.S. Cl.
CPC ................ *A61B 6/035* (2013.01); *A61B 6/58* (2013.01)

(58) Field of Classification Search
CPC .......... A61B 6/4447; A61B 6/035; A61B 6/58
See application file for complete search history.

(56) References Cited

U.S. PATENT DOCUMENTS

| | | | | |
|---|---|---|---|---|
| 2004/0109538 A1* | 6/2004 | McCarthy, Jr. | ...... | A61B 6/4488 378/141 |
| 2005/0013403 A1* | 1/2005 | Reznicek | ................ | G01M 1/32 378/15 |
| 2005/0199059 A1 | 9/2005 | Danz | | |
| 2022/0378384 A1 | 12/2022 | Ji | | |

FOREIGN PATENT DOCUMENTS

CN 216978247 U 7/2022

OTHER PUBLICATIONS

CN 216978247 U and its English translation (Year: 2022).*
CN216978247U English Abstract, Espacenet.com Feb. 26, 2026; 1 page.
JP application 2024-150426 filed Sep. 2, 2024—Office Action issued Dec. 3, 2025; Machine Translation; 4 pages.
EP application 24199976.2 filed Sep. 12, 2024—extended Search Report issued Feb. 6, 2025.

* cited by examiner

*Primary Examiner* — Chih-Cheng Kao

(57) ABSTRACT

Embodiments of the present application provide a data acquisition system assembly, a gantry of a medical imaging system, and a medical imaging system. The data acquisition assembly is disposed in a gantry of a medical imaging system, and includes: a data acquisition system; a first plate, carrying the data acquisition system; a second plate, disposed opposite to the first plate; and a connection portion, disposed between the first plate and the second plate, an end of the connection portion in a height direction being connected to the first plate and the other end of the connection portion in the height direction being connected to the second plate, wherein the dynamic balance of the gantry is adjusted by setting the height and/or the mounting position of the connection portion.

19 Claims, 4 Drawing Sheets

DATA ACQUISITION SYSTEM ASSEMBLY, GANTRY OF MEDICAL IMAGING SYSTEM, AND MEDICAL IMAGING SYSTEM

CROSS-REFERENCE TO RELATED APPLICATIONS

This application claims priority to Chinese Application No. 202311235845.4, filed on Sep. 22, 2023, the disclosure of which is incorporated herein by reference in its entirety.

TECHNICAL FIELD

Embodiments of the present application relate to the technical field of medical devices, in particular to a data acquisition system assembly, a gantry of a medical imaging system, and a medical imaging system.

BACKGROUND

In a computed tomography (CT) imaging system, an X-ray source emits accurately collimated X-rays to a subject under examination, and the X-rays are attenuated by the subject under examination and received by a detector. The detector may be in the form of an array, and each detector element in the array generates a corresponding electrical signal. These electrical signals are transmitted to a data acquisition system for data processing so as to generate a final image.

In a gantry of a CT imaging system, an X-ray source is disposed opposite to a detector. During imaging, the X-ray source and the detector rotate about the Z-axis of the gantry in an imaging plane (X-Y plane). In order to obtain a high-quality image, it is necessary to increase the rotational speed of the X-ray source and the detector. In the case of high-speed rotation, a non-uniform mass distribution of the gantry at respective positions will result in vibrations during the rotation. Such vibrations can affect the service life of components and bearings on the gantry, reducing the image quality.

It should be noted that the above introduction of the background is only for the convenience of clearly and completely describing the technical solutions of the present application, and for the convenience of understanding for those skilled in the art.

SUMMARY

The inventor found that there is a need to replace a detector assembly in some application scenarios. Since the structure and the like of a replacement detector assembly may be different from those of the detector assembly to be replaced, the dynamic balance of the gantry may not be ensured after the replacement, thereby affecting the service life of the gantry and the image quality.

In response to at least one of the above-described technical problems, the embodiments of the present application provide a data acquisition system assembly, a gantry of a medical imaging system, and a medical imaging system.

According to an aspect of the embodiments of the present application, provided is a data acquisition system assembly, disposed in a gantry of a medical imaging system, and including a data acquisition system a first plate carrying the data acquisition system, a second plate disposed opposite to the first plate, and a connection portion, disposed between the first plate and the second plate. An end of the connection portion in a height direction is connected to the first plate and the other end of the connection portion in the height direction is connected to the second plate. The dynamic balance of the gantry is adjusted by setting the height and/or the mounting position of the connection portion.

In some embodiments, the connection portion includes at least one plenum block located at an end position of the first plate or the second plate and at least one connection column located at an intermediate position of the first plate or the second plate.

In some embodiments, in a plane perpendicular to the height direction, the positions and angles of the at least one plenum block and the at least one connection column are symmetrical with respect to a first axis, and the first axis passes through the center of the gantry and the center of the first plate or the second plate.

In some embodiments, the data acquisition system assembly is of an open structure.

In some embodiments, the second plate includes at least one first balance weight plate, and the static balance of the gantry is adjusted by increasing or decreasing the number of the at least one first balance weight plate.

In some embodiments, the at least one first balance weight plate is of a stacked structure.

In some embodiments, the data acquisition system assembly further includes a third plate including at least one second balance weight plate mounted on the first plate or the second plate. The static balance or dynamic balance of the gantry is adjusted by adjusting the at least one second balance weight plate. The weight of the second balance weight plate is less than the weight of the first balance weight plate.

In some embodiments, the second balance weight plate is located at a position farther from the center of the gantry than the second plate.

In some embodiments, the static balance of the gantry is adjusted by increasing or decreasing the number of the at least one second balance weight plate, or the dynamic balance of the gantry is adjusted by adjusting the position of the at least one second balance weight plate in the height direction.

In some embodiments, the gantry includes a rotating portion, and the first plate is detachably connected to the rotating portion of the gantry by means of a universal interface.

According to another aspect of the embodiments of the present application, provided is a gantry of a medical imaging system, including an X-ray source, projecting X-rays, and a detector assembly including a detector and the above-described data acquisition system assembly. The detector detects the X-rays projected by the X-ray source, and the data acquisition system of the data acquisition system assembly performs data processing on a detection result of the detector.

In some embodiments, the gantry includes a rotating portion, and the first plate of the data acquisition system assembly is detachably connected to the rotating portion by means of a universal interface.

According to another aspect of the embodiment of the present application, a medical imaging system is provided. The medical imaging system includes the above-described gantry.

One of the beneficial effects of the embodiments of the present application is that: the data acquisition system assembly is disposed in the gantry of the medical imaging system, and includes the data acquisition system, the first plate carrying the data acquisition system, the second plate disposed opposite to the first plate, and the connection portion connecting the first plate and the second plate, wherein the dynamic balance of the gantry is adjusted by setting the height and/or the mounting position of the connection portion. Thus, the service life of the gantry and the image quality can be ensured.

With reference to the following description and drawings, specific implementations of the embodiments of the present application are disclosed in detail, and the means by which the principles of the embodiments of the present application can be employed are illustrated. It should be understood that the embodiments of the present application are therefore not limited in scope. Within the scope of the spirit and clauses of the appended claims, the embodiments of the present application include many changes, modifications, and equivalents.

BRIEF DESCRIPTION OF THE DRAWINGS

The included drawings are used to provide further understanding of the embodiments of the present application, which constitute a part of the description and are used to illustrate the implementations of the present application and explain the principles of the present application together with textual description. Evidently, the drawings in the following description are merely some embodiments of the present application, and a person of ordinary skill in the art may obtain other implementations according to the drawings without involving inventive effort. In the drawings.

DETAILED DESCRIPTION

Figure 1:
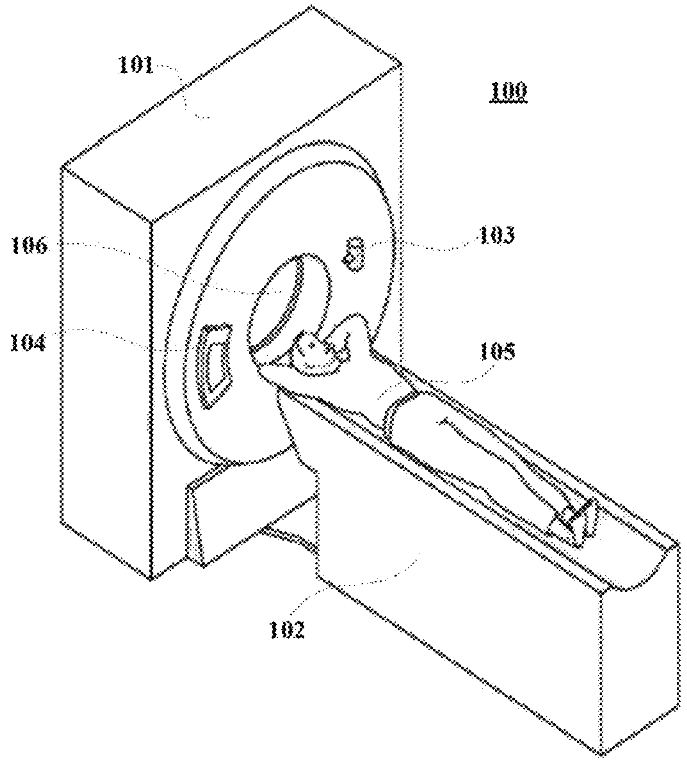
FIG. 1 is a schematic diagram of a CT imaging device according to an embodiment of the present application.

The foregoing and other features of the embodiments of the present application will become apparent from the following description with reference to the drawings. In the description and drawings, specific implementations of the present application are disclosed in detail, and part of the implementations in which the principles of the embodiments of the present application may be employed are indicated. It should be understood that the present application is not limited to the described implementations. On the contrary, the embodiments of the present application include all modifications, variations, and equivalents which fall within the scope of the appended claims.

In the embodiments of the present application, the terms "first", "second", etc., are used to distinguish different elements, but do not represent a spatial arrangement or temporal order, etc., of these elements, and these elements should not be limited by these terms. The term "and/or" includes any and all combinations of one or more associated listed terms. The terms "comprise", "include", "have", etc., refer to the presence of described features, elements, components, or assemblies, but do not exclude the presence or addition of one or more other features, elements, components, or assemblies.

In the embodiments of the present application, the singular forms "a" and "the", etc., include plural forms, and should be broadly construed as "a type of" or "a class of" rather than being limited to the meaning of "one". Furthermore, the term "the" should be construed as including both the singular and plural forms, unless otherwise specified in the context. In addition, the term "according to" should be construed as "at least in part according to . . . " and the term "on the basis of" should be construed as "at least in part on the basis of . . . ", unless otherwise specified in the context.

The features described and/or illustrated for one implementation may be used in one or more other implementations in the same or similar manner, be combined with features in other embodiments, or replace features in other implementations. The terms "include/comprise" when used herein refer to the presence of features, integrated components, steps, or assemblies, but do not preclude the presence or addition of one or more other features, integrated components, steps, or assemblies.

The system for obtaining medical image data (a medical imaging system) described herein includes a medical imaging device. The medical imaging device may be applicable to various medical imaging modalities, including, but not limited to, CT (computed tomography) devices, PET (positron emission tomography)-CT, or any other suitable medical imaging devices.

The medical imaging system may include a separate computer device connected to the medical imaging device, and may also include a computer device connected to an Internet cloud. The computer device is connected via the Internet to the medical imaging device or a memory for storing medical images. An imaging method may be independently or jointly implemented by the aforementioned medical imaging device, the computer device connected to the medical imaging device, and the computer device connected to the Internet cloud.

Exemplarily, the embodiments of the present application are described below in conjunction with an X-ray computed tomography (CT) device. Those skilled in the art would appreciate that the embodiments of the present application can also be applied to other medical imaging devices.

FIG. 1 is a schematic diagram of a CT imaging device according to an embodiment of the present application, and schematically shows a CT imaging device 100. As shown in FIG. 1, the CT imaging device 100 includes a scanning gantry 101 and a patient table 102. The scanning gantry 101 has an X-ray source 103 and a detector assembly 104. The X-ray source 103 is disposed opposite to the detector assembly 104, and the X-ray source 103 projects an X-ray beam toward the detector assembly 104.

A subject under examination 105 can lie flat on the patient table 102 and be moved into a scanning gantry opening 106 along with the patient table 102. The detector assembly 104 receives the X-ray beam projected by the X-ray source 103 and attenuated by the subject under examination 105 to obtain medical image data of the subject under examination 105.

Figure 2:
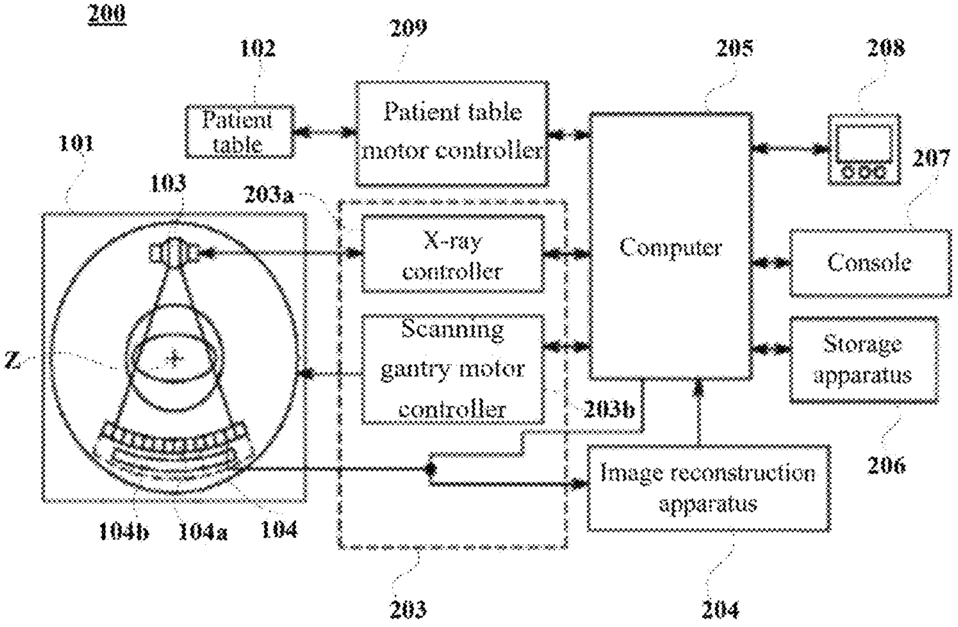
FIG. 2 is a schematic diagram of a CT imaging system according to an embodiment of the present application.

FIG. 2 is a schematic diagram of a CT imaging system according to an embodiment of the present application, and schematically shows a block diagram of a CT imaging system 200. As shown in FIG. 2, the detector assembly 104 includes a detector 104*a* and a data acquisition system (DAS) assembly 104*b*.

The detector 104*a* may be in the form of an array including a plurality of detector units. The plurality of detector units sense projected X-rays passing through the subject under examination 105, and generate electrical signals.

The data acquisition system of the DAS assembly 104*b* performs data processing on a detection result of the detector 104*a*. For example, the data acquisition system receives the electrical signals acquired by the detector 104*a*, and converts these signals into digital signals for subsequent processing. Of course, the function of the data acquisition system is not limited thereto, and sometimes, the data acquisition system also performs a part of subsequent processing. In some designs, the detector 104*a* may also be integrated directly into the data acquisition system.

The scanning gantry 101 includes a fixed portion and a rotating portion that is rotatable with respect to the fixed portion about a central axis (Z-axis) of the gantry. The above-described X-ray source 103 and the detector assembly 104 may be disposed on the rotating portion of the scanning gantry 101. In addition, other components of the CT imaging device, such as a heat exchanger, a collimator, a power supply module, etc., may also be provided on the rotating portion.

During the scanning for acquiring the X-ray projection data, the rotating portion of the scanning gantry 101 drives the components mounted thereon to rotate around the Z axis at a high speed.

The rotation of the scanning gantry 101 and the operation of the X-ray source 103 are controlled by a control mechanism 203 of the CT imaging system 200. The control mechanism 203 includes an X-ray controller 203*a* that provides power and a timing signal to the X-ray source 103 and a scanning gantry motor controller 203*b* that controls the rotational speed and position of the scanning gantry 101.

An image reconstruction apparatus 204 receives the projection data from the DAS assembly 104*b* and performs image reconstruction. A reconstructed image is transmitted as an input to a computer 205, and the computer 205 stores the image in a mass storage apparatus 206.

The computer 205 also receives commands and scanning parameters from an operator by means of a console 207. The console 207 has an operator interface in a certain form, such as a keyboard, a mouse, a voice activated controller, or any other suitable input apparatus. An associated display 208 allows the operator to observe the reconstructed image and other data from the computer 205.

The commands and parameters provided by the operator are used by the computer 205 to provide control signals and information to the DAS assembly 104*b*, the X-ray controller 203*a*, and the scanning gantry motor controller 203*b*. Additionally, the computer 205 operates a patient table motor controller 209 which controls the patient table 102 so as to position the subject under examination 105 and the scanning gantry 101. In particular, the patient table 102 moves the subject under examination 105 in whole or in part to pass through the scanning gantry opening 106 in FIG. 1.

The device and system for acquiring medical image data (which may also be referred to as medical images or medical image data) according to the embodiments of the present application are schematically described above, but the present application is not limited thereto. The medical imaging device may be a CT device, a PET-CT, or any other suitable imaging device. A storage device may be located within the medical imaging device, in a server outside the medical imaging device, in an independent medical imaging storage system (such as a Picture Archiving and Communication System (PACS)), and/or in a remote cloud storage system.

In addition, a medical imaging workstation may be provided locally to the medical imaging device, that is, the medical imaging workstation is provided close to the medical imaging device, and the two may both be located in a scan room, an imaging department, or the same hospital. In contrast, a medical image cloud platform analysis system may be positioned distant from the medical imaging device, e.g., arranged at a cloud end that is in communication with the medical imaging device.

As an example, after a medical institution completes an imaging scan using the medical imaging device, data obtained by scanning is stored in a storage device. A medical imaging workstation may directly read the data obtained by scanning and perform image processing by means of a processor thereof. As another example, the medical image cloud platform analysis system may read a medical image in the storage device by means of remote communication to provide "software as a service (SAAS)". The SAAS may exist between hospitals, between a hospital and an imaging center, or between a hospital and a third-party online diagnosis and treatment service provider.

In an embodiment of the present application, the term "subject" may be equivalently replaced with "subject under examination", "scan subject", "subject to be scanned", "patient", or "subject of study", which may be a human being, an animal, or an object (such as, luggage, etc.). The term "dynamic balance" may be equivalently replaced with "dynamic equilibrium" and "static balance" may be equivalently replaced with "static equilibrium". The term "scanning gantry" may be equivalently replaced with "gantry".

Further, in the following description of the embodiments of the present application, the central axis of a scanning gantry is referred to as a Z axis for the convenience of description; a plane perpendicular to the Z axis is referred to as a rotation plane or an X-Y plane; a direction along or parallel to the Z axis is referred to as an "axial direction"; a radius direction using the Z axis as the center is referred to as a "radial direction"; a direction around the Z axis is referred to as a "circumferential direction"; and a side away from the Z axis in the radius direction is referred to as a "radial outer side", and a side close to the Z axis in the radius direction is referred to as a "radial inner side".

It should be noted that the above directions in the present application are only for the convenience of description of the present application, and are not intended to limit the directions of the data acquisition system assembly, gantry, medical imaging system, and the like of the present application during manufacturing and use.

Figure 3:
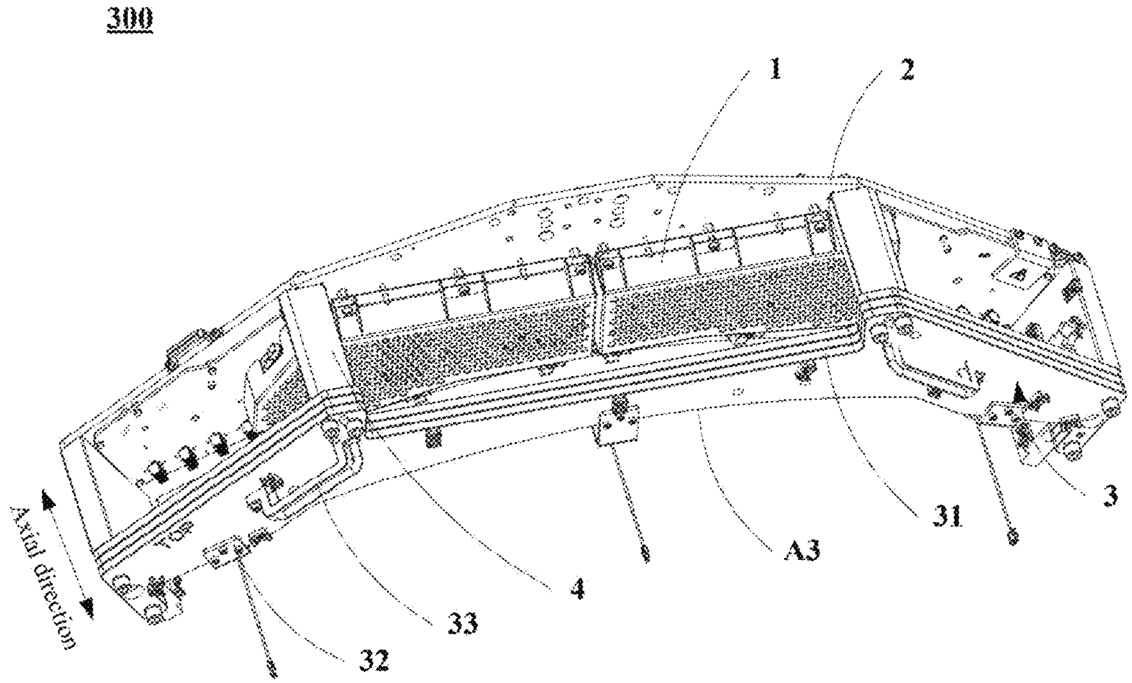
FIG. 3 is a schematic diagram of a data acquisition system assembly according to an embodiment of the present application.

Provided in the embodiments of the present application is a data acquisition system assembly. The data acquisition system assembly is disposed in a gantry of a medical imaging system. FIG. 3 is a schematic diagram of a data acquisition system assembly according to an embodiment of the present application. As shown in FIG. 3, the data acquisition system (DAS) assembly 300 includes: a data acquisition system 1, a first plate 2, a second plate 3, and a connection portion 4.

The first plate 2 carries the data acquisition system 1, the second plate 3 is disposed opposite to the first plate 2, and the connection portion 4 is disposed between the first plate 2 and the second plate 3. One end of the connection portion 4 in a height direction (the axial direction as shown in FIG. 3) is connected to the first plate 2, and the other end of the connection portion 4 in the height direction is connected to the second plate 3. The dynamic balance of the gantry is adjusted by adjusting at least one of the height and the mounting position of the connection portion 4.

According to the above-described embodiments, the data acquisition system assembly 300 is disposed in the gantry of the medical imaging system, and includes the data acquisition system 1, the first plate 2 carrying the data acquisition system, the second plate 3 disposed opposite to the first plate 2, and the connection portion 4 connecting the first plate 2 and the second plate 3, and the dynamic balance of the gantry is adjusted by setting the height of and/or the mounting position of the connection portion 4. Thus, the service life of the gantry and the image quality can be ensured.

As shown in FIG. 3, the first plate 2 and the second plate 3 are disposed opposite to each other in the axial direction, and the distance between the first plate 2 and the second plate 3 can be adjusted by increasing or decreasing the height of the connection portion 4, thereby adjusting the mass distribution of the DAS assembly 300 in the axial direction. When the height of the connection portion 4 is set to an appropriate height, the mass distribution of the gantry in the axial direction can be uniform, so that the gantry reaches a state of dynamic balance. In addition, the mass distribution of the DAS assembly 300 may also be adjusted by adjusting the mounting position of the connection portion 4, so that the gantry reaches a state of dynamic balance.

In some embodiments, the mass distribution of the DAS assembly 300 in the axial direction is related to the mass distribution of an X-ray source (e.g., the aforementioned X-ray source 103) opposite thereto. For example, in an ideal case, it is desirable that the centroid positions of the DAS assembly 300 and the X-ray source in planes perpendicular to the axial direction are at the center of the gantry. The present application is not limited thereto, and the gantry may be considered to reach a state of dynamic balance as long as appropriate stability can be ensured for the rotation of the gantry and the image quality satisfies a preset requirement.

In some embodiments, the data acquisition system 1 may be implemented in various ways. For example, the data acquisition system 1 may include a circuit board or the like having electronic devices. The data acquisition system 1 may be mounted on the first plate 2 in various ways. For example, the data acquisition system is mounted on the first plate 2 by means of a fixing component which may be, for example, a screw, or mounted on the first plate 2 by means of welding, engagement, or the like.

Figure 4:
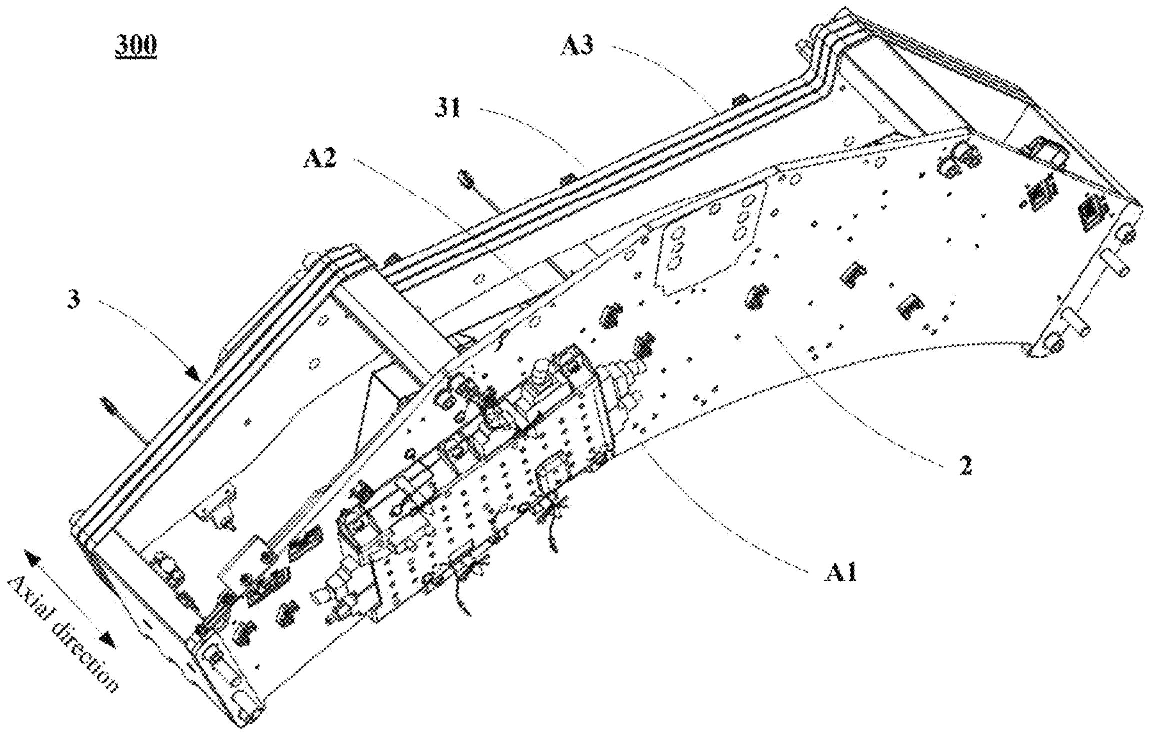
FIG. 4 is another schematic diagram of a data acquisition system assembly according to an embodiment of the present application.

FIG. 4 is another schematic diagram of a data acquisition system assembly according to an embodiment of the present application. As shown in FIG. 4, the first plate 2 is plate-shaped, and is provided with a plurality of mounting holes. Some of the mounting holes may be, for example, holes for mounting the data acquisition system 1.

In some embodiments, the first plate 2 may also be provided with an interface connected to the rotating portion of the gantry. As a result, the DAS assembly 300 can be mounted at the rotating portion of the gantry, and when the rotating portion rotates, the DAS assembly 300 is driven to rotate. In some embodiments, the connection between the first plate 2 and the rotating portion may be a detachable connection. Thus, it is easy to replace and perform maintenance on the DAS assembly 300. In some embodiments, the interface of the first plate 2 connected to the rotating portion may be a universal interface. Thus, the DAS assembly 300 may be mounted at a rotating portion of a different gantry, or a different model of the DAS assembly 300 may be mounted at the rotating portion of the same gantry.

For example, a user may replace a 64-row detector assembly with a 32-row detector assembly, wherein the 64-row detector assembly includes 64 rows of detectors and DAS assemblies corresponding to the 64 rows of detectors, and the 32-row detector assembly includes 32 rows of detectors and DAS assemblies corresponding to the 32 rows of detectors. Since the height and/or the mounting position of the connection portion 4 of the DAS assembly 300 in the 32-row detector assembly is appropriate, the gantry can also reach a dynamic balance after replacement of the detector assembly. Thus, the process of replacing the assembly inside the gantry can be simplified, thereby facilitating the on-site replacement of the assembly, and improving user experience.

In some embodiments, as shown in FIG. 4, a radial inner side edge A1 of the first plate 2 may be substantially arc-shaped, and thus, can match a detector that is also arc-shaped, so that the first plate 2 does not interfere with the detector.

In some embodiments, as shown in FIG. 4, a radial outer side edge A2 of the first plate 2 may have a polygonal shape. The present application is not limited thereto, and the specific shape of the edge A2 may be related to the layout of the components mounted on the first plate 2. In some embodiments, the first plate 2 may have an axisymmetric shape, and the axis of symmetry extends in the radial direction. Configuring the first plate 2 to be in an axisymmetric shape helps to uniformly distribute the mass of the DAS assembly 300 in the circumferential direction. In some embodiments, as shown in FIGS. 3 and 4, the second plate 3 may include at least one first balance weight plate 31. The static balance of the gantry is adjusted by increasing or decreasing the number of the at least one first balance weight plate.

As shown in FIGS. 3 and 4, the mass distribution of the DAS assembly 300 in the circumferential direction can be adjusted by increasing or decreasing the number of the first balance weight plates 31. When the number of the first balance weight plates 31 is set to an appropriate number, the mass distribution of the gantry in the circumferential direction can be uniform, so that the gantry reaches a state of static balance.

In some embodiments, the at least one first balance weight plate 31 may be of a stacked structure, and thus it is easy to adjust the number of the first balance weight plates 31. As shown in FIGS. 3 and 4, the second plate 3 may include three first balance weight plates 31 arranged in a stack. The present application is not limited thereto, and the first balance weight plate 31 may be provided in another number or configured in another manner.

In some embodiments, as shown in FIGS. 3 and 4, an edge A3 of the first balance weight plate 31 may have a polygonal shape. The present application is not limited thereto, and the specific shape of the edge A3 may be related to the layout of the components mounted on the first plate 2 and the position of the connection portion 4.

In some embodiments, the second plate 3 may have an axisymmetric shape, and the axis of symmetry extends in the radial direction. Configuring the second plate 3 to be in an axisymmetric shape helps to uniformly distribute the mass of the DAS assembly 300 in the circumferential direction.

In some embodiments, as shown in FIG. 3, the second plate may carry a sensor 32. The sensor 32 may be a temperature sensor used to measure the temperature in the vicinity of the DAS assembly 300. The present application is not limited thereto, and the sensor 32 may also be a speed sensor or the like used to measure the rotational speed of the DAS assembly 300. In some embodiments, as shown in FIG. 3, the second plate 3 may be provided with a handle 33, and thus it is easy to adjust the number of the first balance weight plates 31.

Figure 5:
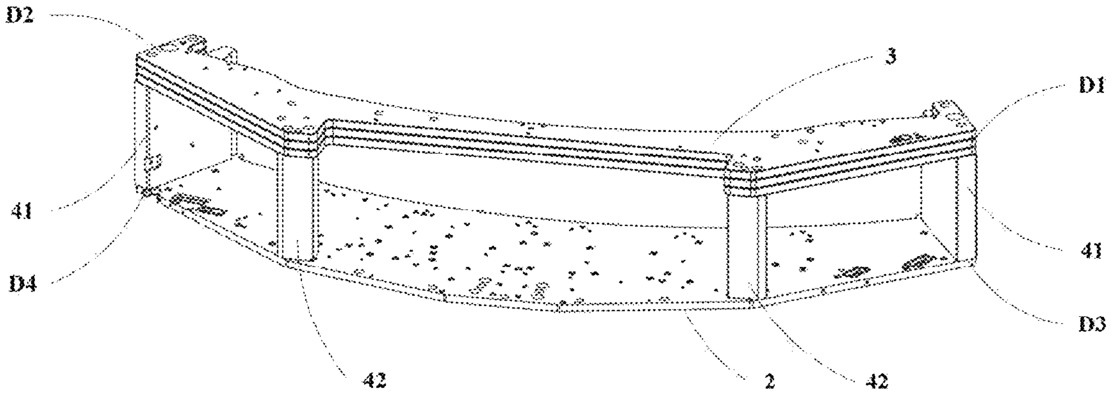
FIG. 5 is a schematic diagram of a first plate, a second plate, and a connection portion according to an embodiment of the present application.
Figure 6:
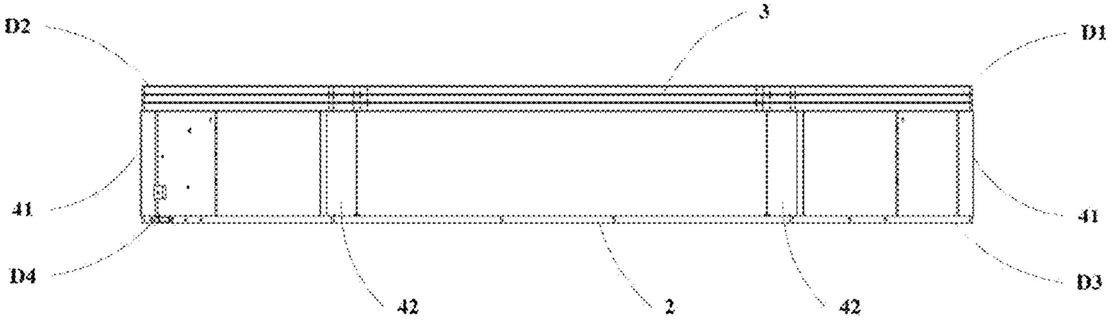
FIG. 6 is another schematic diagram of a first plate, a second plate, and a connection portion according to an embodiment of the present application.

FIG. 5 and FIG. 6 are schematic diagrams of the first plate 2, the second plate 3, and the connection portion 4 according to an embodiment of the present application. In some embodiments, a plurality of connection portions 4 may be provided, whereby the connection strength of the first plate 2 and the second plate 3 can be ensured.

For example, as shown in FIGS. 5 and 6, the connection portion 4 may include at least one plenum block 41 located at ends D1 and D2 of the first plate 2 or ends D3 and D4 of the second plate 3, and at least one connection column 42 located at an intermediate position of the first plate 2 or the second plate 3. By arranging the connection portion 4 at the ends and the middle position of the first plate 2 or the second plate 3, the connecting strength of the first plate 2 and the second plate 3 can be ensured.

In some embodiments, the plenum block 41 may be substantially plate-shaped and the connection column 42 may be substantially cylindrical. By disposing the plenum block 41 at the end position, the connection area for the first plate 2 and the second plate 3 can be increased, so that connection strength can be further provided. By disposing the connection column 42 having a relatively small cross-sectional area at the intermediate position, it is possible to avoid interference of the connection column 42 with other components mounted on the first plate 2, thereby facilitating the arrangement of the other components.

In some embodiments, in the plane perpendicular to the height direction (an axial direction), the positions and angles of the at least one plenum block 41 and the at least one connection column 42 are symmetrical with respect to a first axis, and the first axis passes through the center of the gantry and the center of the first plate 2 or the second plate 3. In other words, the first axis may extend in the radial direction. Configuring the positions and angles of the plenum block 41 and the connection column 42 to be axisymmetric helps to uniformly distribute the mass of the DAS assembly 300 in the circumferential direction.

The present application is not limited thereto. The plenum block 41 and the connection column 42 may also be disposed at other positions, or the connection portion 4 may include only the plenum block 41 or the connection column 42, or the connection portion 4 may also have other forms.

In some embodiments, the connection portion 4 may be connected to the first plate 2 and the second plate 3 in various ways. For example, the connection portion 4 is connected to the first plate 2 and the second plate 3 by means of a fixing component which may be, for example, a screw or the like. Alternatively, the connection portion 4 is connected to the first plate 2 and the second plate 3 by means of welding, engagement, or the like.

In some embodiments, the DAS assembly 300 may be of an open structure, thereby facilitating ventilation and heat dissipation for the data acquisition system or other internal components of the DAS assembly 300. As shown in FIG. 5 and FIG. 6, adjacent plenum blocks 41, or adjacent connection columns 42, or adjacent plenum blocks 41 and connection columns 42 are spaced apart from each other, thereby forming an open structure. When the DAS assembly 300 rotates with the rotating portion of the gantry, heat can be dissipated for the circuit board of the data acquisition system by means of natural wind.

Figure 7:
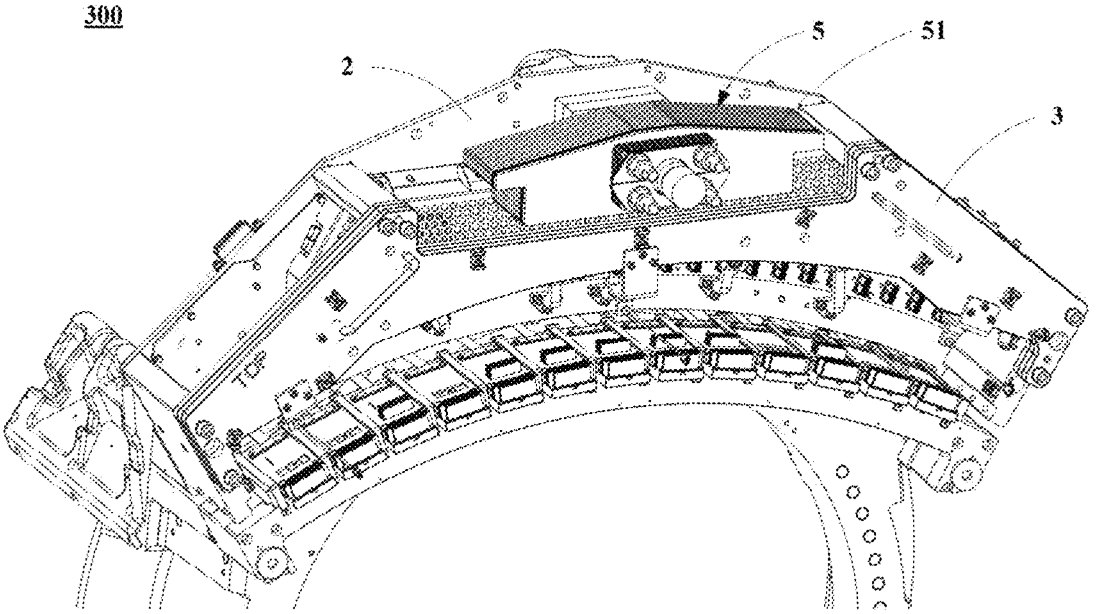
FIG. 7 is another schematic diagram of a data acquisition system assembly according to an embodiment of the present application.

FIG. 7 is another schematic diagram of the DAS assembly 300 according to an embodiment of the present application. As shown in FIG. 7, the data acquisition system assembly 300 may also include a third plate 5. The third plate 5 includes at least one second balance weight plate 51 mounted on the first plate 2 or the second plate 3, and the static balance or the dynamic balance of the gantry is adjusted by adjusting the at least one second balance weight plate 51, wherein the weight of the second balance weight plate 51 is less than the weight of the first balance weight plate 31. The third plate 5 is provided, so that the static balance and the dynamic balance of the gantry can be adjusted more precisely.

In some embodiments, the static balance of the gantry may be adjusted by increasing or decreasing the number of the at least one second balance weight plate 51. In some embodiments, the dynamic balance of the gantry may be adjusted by adjusting the position of the at least one second balance weight plate 51 in the height direction. For example, when the DAS assembly 300 is designed and manufactured, by adjusting the number of the first balance weight plates 31 and the height and/or the mounting position of the connection portion 4, the DAS assembly 300 satisfies the requirements for the static balance and the dynamic balance of the gantry. However, at the site where the DAS assembly 300 is to be mounted or replaced, the original static balance or dynamic balance may be disrupted due to the influence of uncertain factors such as the position of a cable. In this case, the influence of the above-mentioned uncertain factors on the static balance and the dynamic balance of the gantry can be eliminated by making more precise adjustment by means of changing the number or the configured height of the second balance weight plate 51 having a relatively light weight.

In some embodiments, as shown in FIG. 7, the second balance weight plate 51 may be located at a position further away from the center of the gantry than the second plate 3. Thus, the second balance weight plate 51 can be prevented from interfering with other components. The present application is not limited thereto, and the second balance weight plate 51 may be located at other positions.

It is worth noting that only the individual components or modules relevant to this embodiment have been described above, but the present application is not limited thereto. The data acquisition system assembly may also include other components or modules, and reference may be made to the related art for details of these components or modules.

In addition, for the sake of simplicity, FIGS. 1 to 7 only exemplarily illustrate the connection or position relationship between various components or modules, but it should be clear to those skilled in the art that various related technologies such as mechanical connection or bus connection can be used for the various components or modules. The above-described various components or modules can be implemented by means of hardware or mechanical structures such as electronic devices, processors, memories, transmitters, receivers, etc. The embodiments of the present application are not limited thereto.

According to the embodiments of the present application, the data acquisition system assembly 300 is disposed in the gantry of the medical imaging system, and includes the data acquisition system 1, the first plate 2 carrying the data acquisition system, the second plate 3 disposed opposite to the first plate 2, and the connection portion 4 connecting the first plate 2 and the second plate 3, and the dynamic balance of the gantry is adjusted by setting the height and/or the mounting position of the connection portion 4. Thus, the service life of the gantry and the image quality can be ensured.

Provided in the embodiments of the present application is a gantry of a medical imaging system, which includes the data acquisition system assembly 300 as described in the embodiment of the first aspect. In the embodiments of the first aspect, the structure of the data acquisition system assembly 300 is described in detail, the content of which is incorporated herein, and will not be further described.

Figure 8:
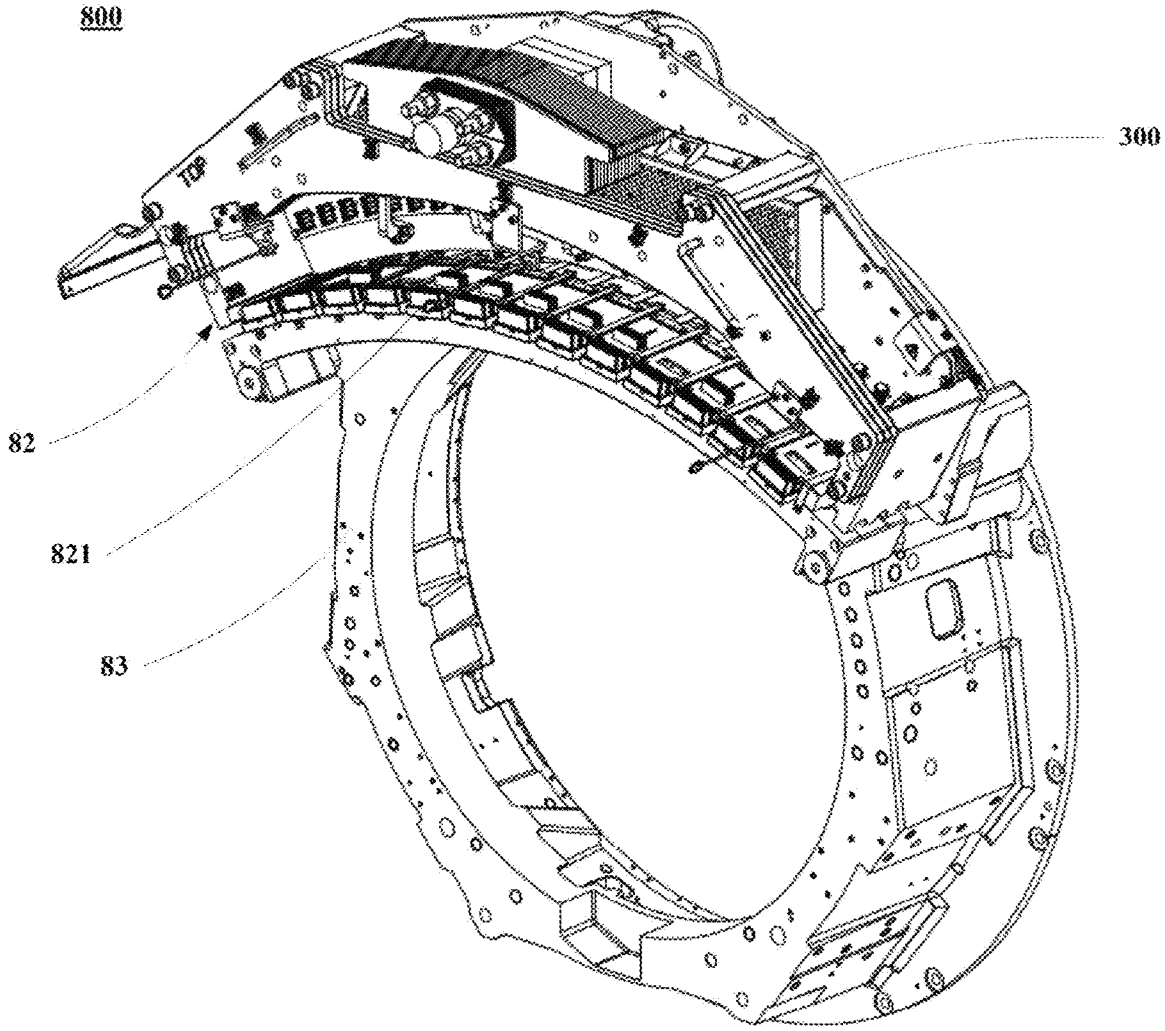
FIG. 8 is a schematic diagram of a gantry of a medical imaging system according to an embodiment of the present application.

FIG. 8 is a schematic diagram of a gantry 800 of a medical imaging system according to an embodiment of the present application. As shown in FIG. 8, the gantry 800 includes an X-ray source (not shown) and a detector assembly 82. The X-ray source projects X-rays. The X-ray source is, for example, the aforementioned X-ray source 103. The detector assembly 82 may include a detector 821 and the aforementioned data acquisition system assembly 300. The detector 821 detects the X-rays projected by the X-ray source, and the data acquisition system of the data acquisition system assembly 300 performs data processing on a detection result of the detector 821.

In some embodiments, as shown in FIG. 8, the gantry 800 includes a rotating portion 83, and the first plate of the data acquisition system assembly 300 is detachably connected to the rotating portion 83 by means of a universal interface. It should be noted that FIG. 8 is merely a specific example of the gantry 800. The gantry 800 may also include other components not shown in FIG. 8, which are not limited in the embodiments of the present application. Reference may be made to the related art for the other components.

According to an embodiment of the present application, the gantry 800 includes the data acquisition system assembly 300 described in the first aspect, the data acquisition system assembly 300 includes the data acquisition system 1, the first plate 2 carrying the data acquisition system, the second plate 3 disposed opposite to the first plate 2, and the connection portion 4 connecting the first plate 2 and the second plate 3, and the dynamic balance of the gantry is adjusted by setting the height and/or the mounting position of the connection portion 4. Thus, the service life of the gantry 800 and the image quality can be ensured.

Provided in the embodiments of the present application is a medical imaging system. The configuration of the medical imaging system is as shown in FIG. 2, and a repeated description will not be provided again. The medical imaging system includes the gantry 800 as described in the embodiments of the second aspect, the content of which is incorporated herein.

According to an embodiment of the present application, the medical imaging system includes the gantry 800 described in the second aspect, the gantry 800 includes the data acquisition system assembly 300 described in the embodiments of the first aspect, the data acquisition system assembly 300 includes the data acquisition system 1, the first plate 2 carrying the data acquisition system, the second plate 3 disposed opposite to the first plate 2, and the connection portion 4 connecting the first plate 2 and the second plate 3, and the dynamic balance of the gantry is adjusted by setting the height and/or the mounting position of the connection portion 4. Thus, the service life of the gantry 800 and the image quality can be ensured. Furthermore, the service life and image quality of the medical imaging system can be guaranteed.

The above embodiments merely provide illustrative descriptions of the embodiments of the present application. However, the present application is not limited thereto, and appropriate variations may be made on the basis of the above embodiments. For example, each of the above embodiments may be used independently, or one or more among the above embodiments may be combined.

The present application is described above with reference to specific embodiments. However, it should be clear to those skilled in the art that the foregoing description is merely illustrative and is not intended to limit the scope of protection of the present application. Various variations and modifications may be made by those skilled in the art according to the spirit and principle of the present application, and these variations and modifications also fall within the scope of the present application.

Preferred embodiments of the present application are described above with reference to the accompanying drawings. Many features and advantages of the implementations are clear according to the detailed description, and therefore the appended claims are intended to cover all these features and advantages that fall within the true spirit and scope of these implementations. In addition, as many modifications and changes could be easily conceived of by those skilled in the art, the embodiments of the present application are not limited to the illustrated and described precise structures and operations, but can encompass all appropriate modifications, changes, and equivalents that fall within the scope of the implementations.

The invention claimed is:

1. A data acquisition system assembly, disposed in a gantry of a medical imaging system, and characterized by comprising:

a data acquisition system;

a first plate carrying the data acquisition system;

a second plate disposed opposite to the first plate; and a connection portion, disposed between the first plate and the second plate, an end of the connection portion in a height direction being connected to the first plate and the other end of the connection portion in the height direction being connected to the second plate, wherein the dynamic balance of the gantry is adjusted by setting the height and/or the mounting position of the connection portion, wherein the connection portion includes at least one plenum block located at an end position of the first plate or the second plate and at least one connection column located at an intermediate position of the first plate or the second plate.

2. The data acquisition system assembly according to claim 1, wherein in a plane perpendicular to the height direction, the positions and angles of the at least one plenum block and the at least one connection column are symmetrical with respect to a first axis, and the first axis passes through the center of the gantry and the center of the first plate or the second plate.

3. The data acquisition system assembly according to claim 1, wherein the data acquisition system assembly is of an open structure.

4. The data acquisition system assembly according to claim 1, wherein the second plate includes at least one first balance weight plate, and the static balance of the gantry is adjusted by increasing or decreasing the number of the at least one first balance weight plate.

5. The data acquisition system assembly according to claim 4, wherein the at least one first balance weight plate is of a stacked structure.

6. The data acquisition system assembly according to claim 4, further including a third plate including at least one second balance weight plate mounted on the first plate or the second plate, the static balance or dynamic balance of the gantry being adjusted by adjusting the at least one second balance weight plate, wherein the weight of the second balance weight plate is less than the weight of the first balance weight plate.

7. The data acquisition system assembly according to claim 6, wherein the second balance weight plate is located at a position farther from the center of the gantry than the second plate.

8. The data acquisition system assembly according to claim 6, wherein:

the static balance of the gantry is adjusted by increasing or decreasing the number of the at least one second balance weight plate; or, the dynamic balance of the gantry is adjusted by adjusting the position of the at least one second balance weight plate in the height direction.

9. The data acquisition system assembly according to claim 1, wherein the gantry includes a rotating portion, and the first plate is detachably connected to the rotating portion of the gantry by means of a universal interface.

10. A data acquisition system assembly, disposed in a gantry of a medical imaging system, and characterized by comprising:

a data acquisition system;

a first plate carrying the data acquisition system;

a second plate disposed opposite to the first plate; and a connection portion, disposed between the first plate and the second plate, an end of the connection portion in a height direction being connected to the first plate and the other end of the connection portion in the height direction being connected to the second plate, wherein the dynamic balance of the gantry is adjusted by setting the height, the mounting position of the connection portion, or a combination thereof, wherein the connection portion includes at least one plenum block located proximate to the first plate and the second plate.

11. The data acquisition system assembly according to claim 10, wherein the connection portion includes at least one connection column located at an intermediate position of the first plate or the second plate.

12. The data acquisition system assembly according to claim 11, wherein in a plane perpendicular to the height direction, the positions and angles of the at least one plenum block and the at least one connection column are symmetrical with respect to a first axis, and the first axis passes through the center of the gantry and the center of the first plate or the second plate.

13. The data acquisition system assembly according to claim 10, wherein the data acquisition system assembly is of an open structure.

14. The data acquisition system assembly according to claim 10, wherein the second plate includes at least one first balance weight plate, and the static balance of the gantry is adjusted by increasing or decreasing the number of the at least one first balance weight plate.

15. The data acquisition system assembly according to claim 14, wherein the at least one first balance weight plate is of a stacked structure.

16. The data acquisition system assembly according to claim 14, further including a third plate including at least one second balance weight plate mounted on the first plate or the second plate, the static balance or dynamic balance of the gantry being adjusted by adjusting the at least one second balance weight plate, wherein the weight of the second balance weight plate is less than the weight of the first balance weight plate.

17. The data acquisition system assembly according to claim 16, wherein the second balance weight plate is located at a position farther from the center of the gantry than the second plate.

18. The data acquisition system assembly according to claim 16, wherein:

the static balance of the gantry is adjusted by increasing or decreasing the number of the at least one second balance weight plate; or, the dynamic balance of the gantry is adjusted by adjusting the position of the at least one second balance weight plate in the height direction.

19. The data acquisition system assembly according to claim 10, wherein the gantry includes a rotating portion, and the first plate is detachably connected to the rotating portion of the gantry by means of a universal interface.

* * * * *